United States Patent [19]

Fulger et al.

[11] Patent Number: 4,752,482
[45] Date of Patent: * Jun. 21, 1988

[54] PROCESS FOR PREPARING A HEAT STABLE FERMENTED MALT FLAVORANT

[75] Inventors: Charles V. Fulger, Katonah; Wen C. Lou, Yorktown Heights, both of N.Y.

[73] Assignee: General Foods Corp., White Plains, N.Y.

[ * ] Notice: The portion of the term of this patent subsequent to May 5, 2004 has been disclaimed.

[21] Appl. No.: 16,029

[22] Filed: Feb. 18, 1987

Related U.S. Application Data

[63] Continuation-in-part of Ser. No. 758,892, Jul. 25, 1985, Pat. No. 4,663,168.

[51] Int. Cl.[4] ................................................. A23L 1/22
[52] U.S. Cl. ....................................... 426/28; 426/18; 426/20; 426/533
[58] Field of Search ...................... 426/28, 20, 18, 533

[56] References Cited

U.S. PATENT DOCUMENTS

| | | | |
|---|---|---|---|
| 2,916,382 | 12/1959 | Morton et al. | 426/533 |
| 3,102,815 | 9/1963 | Spotholz et al. | 426/533 |
| 3,102,816 | 9/1963 | Green et al. | 426/533 X |
| 3,102,817 | 9/1963 | Green | 426/533 |
| 3,316,099 | 4/1967 | Hoersch | 426/533 |
| 4,045,587 | 8/1977 | Katz et al. | 426/533 |
| 4,089,978 | 5/1978 | Lugay et al. | 426/533 X |
| 4,663,168 | 5/1987 | Fulger et al. | 426/228 |

*Primary Examiner*—Joseph Golian
*Attorney, Agent, or Firm*—Thomas A. Marcoux; Thomas R. Savoie; Daniel J. Donovan

[57] ABSTRACT

A process is disclosed for producing a heat-stable, yeast fermented malt reaction flavor concentrate which is of low volatility. The process involves preparing a malt flour such that it has sufficient fermentable sugars, fermenting the malt flour with yeast at a temperature of from about 10° C. to about 60° C. for a period of time of from ½ to 6 hours and heating the fermented malt produced by the fermentation to inactive the yeast and develop flavors. The yeast fermented malt derived food flavorant may be incorporated into a foodstuff, preferably a ready-to-eat cereal or baked good at a level of from 0.3 to 5% by weight.

15 Claims, No Drawings

PROCESS FOR PREPARING A HEAT STABLE FERMENTED MALT FLAVORANT

This application is a continuation-in-part of our co-pending U.S. application Ser. No. 758,892, filed July 25, 1985, now U.S. Pat. No. 4,663,168.

TECHNICAL FIELD

The present invention relates to the field of food flavorants and more specifically to the production of a strong, heat-stable, bready and cooked grain flavor which is especially useful for flavoring extruded food materials such as cereal products produced by short time, high temperature processing in a cooker extruder.

BACKGROUND ART

Recent advances in the food art, i.e. in the art of extrusion, permit the short time preparation of extruded dough products which have desirable texture, functionality (i.e. rate of hydration and hydrated texture retention rate) and certain organoleptic characteristics. However these products lack sufficient flavor. The longer-time, traditionally manufactured food products were more flavorful because the longer cooking times that were employed permitted greater development of flavor and flavor precursors through the various reactions taking place during the long cooking, drying and toasting times. For example, traditionally manufactured puffed cereal products were produced by a process which included batch cooking, tunnel drying, tempering, pelletizing and gun puffing all of which together took approximately several hours. Today's modern technological innovations permit the production of a direct-expanded cereal product in a period of time of less than one minute by direct expansion in a cooker extruder. While the two processes utilize the same ingredients, the traditional process leads to the production of a more flavorful product. Similarly, other products like flaked, cooked grains lack flavor when extruder processed.

In order to compensate for the flavor difficiencies of the modern processed foodstuffs, the food art has strived to invent new flavorants which would augment or enhance particular flavors. U.S. Pat. No. 3,615,697 issued to Hollenbeck teaches a food flavor which is prepared by fermenting malt flour with a lactic acid producing microorganism. The dried product combines malt flavor with the sour taste of lactic acid and related fermented flavors. The flavor may be added to a variety of baked goods such as bread, as well as dried, ready-to-eat cereals. More specifically, the patent discloses a process wherein cottage cheese whey is added to live lactobacillus bacteria, and thereafter malt which is then fermented to form a heat-labile, volatile flavor as an alternate process to produce sour dough bread.

It is an object of the present invention to form a concentrated food flavorant which duplicates typical cooked grain type flavors and which can be added to high temperature, short time processed foods without heat degredation to improve their taste and flavor.

DISCLOSURE OF THE INVENTION

The present invention relates to a process for producing a heat-stable, low volatile, yeast fermented malt reaction flavor concentrate from a malt flour. The process involves preparing malt flour for yeast fermentation such that the malt flour will have sufficient fermentable sugars for the yeast to metabolize. Thereafter, the malt flour, now containing sufficient fermentable sugars, is subjected to yeast fermentation at a temperature of from about 10° C. to about 60° C. for a period of time ranging from about ½ hour to about 6 hours. Thereafter the fermented malt produced by the yeast fermentation is heated at a temperature and for a time sufficient to inactivate the yeast and any residual enzymes present and to develop a desirable flavor. The developed reaction flavor can be characterized as primarily a condensation flavor product which explains its observed heat stability. The yeast fermented reaction flavor concentrate which is produced according to the present invention is heat stable and of low volatility which makes it especially desirable for incorporation into processed foods produced by high temperature short time cooker extrusion such as baked goods and ready-to-eat breakfast cereals. When the flavorant is added to a foodstuff it duplicates typical cooked grain type flavors of the type that were characteristically developed by long time grain cooking processes like cereal cooking and baking.

BEST MODE FOR CARRYING OUT THE INVENTION

The present invention describes a process for producing a yeast fermented malt derived flavorant. The first step of this process involves taking a malt flour and preparing it for yeast reaction. Preferably the malt flour should be debranned, since the bran content of the malt may lead to the development of off-flavors and a bitter taste. Thereafter the malt flour should be milled, typically to a particle size of from about 20 to about 400 microns and thereafter the milled malt flour should be steeped in water to hydrate the flour. Typically a mixture of malt flour in water should be of a concentration of from about 20 to about 70 percent solids and preferably 25 to 40 percent solids. At this point in the process, a so called sponge is created from the high moisture hydrated mixture of the malt flour. It becomes necessary to have present within this sponge or dough a sufficient amount of fermentable sugars for yeast fermentation. The amount of fermentable sugars that must be present within the malt flour to permit yeast fermentation will vary from 6 to 30%, preferably from 10 to 20% dry weight basis of the malt flour. (Fermentable sugar content was assayed by gas chromatography of oxime-TMS-derivatives of sugars, on JNW, DB-1 FSOT columns.) This may be accomplished by one of four different methods depending upon the type of malt utilized and the processes employed to produce the malt. In the first of these options, a malt product which contains endogenous enzymes may be steeped at a temperature of about 30° C. to about 45° C. for about 30 minutes to 150 minutes to allow for the endogenous enzymes to hydrolyze the starch present in the malt flour. This option will work well with a malt flour that will contain a high enzyme level, such as a malt flour which was produced by a process which did not inactivate the endogenous enzymes. If a temperature lower than the 30° C. is utilized in the hydrolysis reaction, the reaction time will be slowed to such an extent as to make the process commercially unattractive and if the temperature exceeds the 45° C. limitation it will lead to inactivation of the enzyme.

The second processing method to assure that the malt flour will possess sufficient fermentable sugars is utilized in a situation where the malt does not possess sufficient endogenous enzymes, sufficient fermentable carbohydrates or for other reasons it is not considered desirable to utilize the endogenous hydrolysis method. In this case, malt, preferably one which has been debranned is steeped in water to form the dough or sponge previously described. To this dough or sponge is added exogenous glycolytic enzymes which will hydrolyze starch present within the malt flour to yield sufficient fermentable sugars for the yeast fermentation. The preferable process utilizes alpha amylase followed by glucoamylase or the combination of alpha amylase and glucoamylase. Before the exogenous enzymes are added to the malt, the starch within the malt flour is gelatinized. It is preferable to gelatinize the starch by one or more methods known in the prior art. Typically, such processes would involve heating the malt flour by steam injection in a jet cooker at about 140° C. to about 165° C. with or without the addition of a thermally stable alpha amylase (to make a more flowable mixture) for a period of time varying from one second to 30 seconds. The times and temperatures necessary for the exogenous enzymatic hydrolysis would be similar to those discussed in the first processing option.

The third processing option which would prepare the malt for yeast fermentation by assuring sufficient fermentable sugars would be to disregard the use of enzymes all together, whether they be endogenous enzymes present within the malt or exogenously added enzymes. This option involves the simple addition of exogenous fermentable sugars. Typically the level of addition would vary from 6 to 30 percent dry weight basis of the malt flour and preferably from 10 to 20 percent.

The fourth processing option to assure sufficient fermentable sugars within the malt-flour would be to use caramel malt which is known to contain up to about 20%, typically from 10% to 18% fermentable sugars developed naturally in the malting process. This processing option would require neither the use of exogenous enzymes nor endogenous malt enzymes.

After the malt has been prepared according to one of the four processing options discussed, the steeped malt flour is subjected to yeast fermentation. The milled malt in a dough or sponge of from 20 to 70 percent solids concentration preferably from 25 to 40 percent is subjected to yeast fermentation which acts to change the existing metabolites in the malt thereby creating new flavors and flavor precursors both by the yeast enzymes and by the autolysis of the yeast. By selecting time and temperature variables during the yeast fermentation, it is possible to control the amount and kind of flavorant which is produced. The malt flour slurry during yeast fermentation will be maintained at a temperature within the range of 10° C. to 60° C., preferably from 20° C. to 35° C., for a period of time ranging from approximately ½ hour to 6 hours, preferably from 2 to 4 hours. The amount of time depends upon the amount and type of yeast utilized and the amount of fermentable sugars present within the malt. The concentration of yeast which would be incorporated into the malt flour slurry will vary from approximately 0.5 percent to approximately 10 percent (dry basis), preferably from 1 to 7 percent and most preferably 2 to 5 percent. It is known in the art that various yeast strains and species have different fermentation characteristics and produce different metabolites. While the overall functionality and metabolites are similar to each other, these differences can be taken advantage of in tailoring the end product flavor profile. Typically the malt flour in a dough or sponge of approximately 30 percent solids will be contacted for about 2 hours with 2 percent yeast. The type of yeast utilized can consist of either compressed yeast or active dry yeast. For example, it was found that for flavoring direct expanded cereal feedstocks, Saccharomyce cerevisiae was an effective in producing reaction flavor precursors on hydrolyzed malt flour. Also, other types of yeast such as S. elipseus or S. carlsbergensis can be utilized. The yeast is prepared into its active form according to methods known in the prior art. In addition to the yeast, lesser amounts of other flavor producing microorganisms may be added, i.e., Acetobacterium sp., Propionibacterium sp., etc., to develop other types of flavor precursors.

After the yeast fermentation has been accomplished the last step in the process of the present invention involves heating the fermented malt to accomplish a dual purpose of inactivating the yeast and other enzymes present within the sponge or dough and to effect flavor development. The preferable way to accomplish the heating is to dry and then toast the sponge or dough in a short time manner of from about 5 to about 30 seconds utilizing high temperatures on hot surfaces within the temperature range of from about 135° C. to about 200° C. The most optimal way to accomplish this type of drying is by drum drying. During this drying process, the water is first evaporated and thereafter separately or continuously upon exposure to the high temperature a series of chemical reactions takes place within the fermented malt. These reactions include condensation reactions, Maillard type (amine and aldehyde group reactions) browning reactions, esterification reactions, oxidative reactions, etc. Typically the toasted fermented malts contain less than about 5 percent moisture.

Rather than drying and toasting the fermented malt product, the sponge or dough can be subjected to a high temperature, high pressure autoclave which will inactivate the enzymes and autolyze the yeast and cause reactions between the metabolites in the sponge or dough. This autoclaving is accomplished at a temperature of from about 120° C. to about 200° C. for a period of time ranging from approximately 3 to 45 minutes. The autoclaved product can be used as is by incorporating it into a convenient step in a cereal or bakery manufacturing process or it can be dried to a moisture content typically around 10 percent with or without a drying aid such as flour or starch according to processes known in the art. In this procedure, the flavor can be developed during the high temperature treatment that takes place during the manufacture of certain breakfast cereals, i.e. during rotary cooking, hot flaking, toasting and/or autoclaving.

The process of the present invention can be carried out on a malt flour derived from a grain which is either rye, barley, wheat, or a combination of this grains. The preferable malted grain flour for the present invention is barley malt flour since the barley malt is highly flavorful. In addition to the malted grain flour a lesser amount of a nongrain (non-graminaceae) seed material can be incorporated. Examples of these materials include buckwheat, sorghum, corn, and milo.

As will be recognized by those skilled in the art, the pH during the process needs to be adjusted for optimal reactions to occur, especially if enzymes are utilized in the treatment of the malt and for optimal flavor development during the heating/drying step. It is also well known that the yeast has a broad range of compatible pH's.

The fermented malt derived food flavorant of the present invention is heat-stable and has a low volatility and may be incorporated into a wide variety of food products at a level of from approximately 0.3 percent to 5 percent dry weight basis, preferably from 1 percent to 3.5 percent. The fermented malt derived food flavorant of the present invention will have its greatest application in ready-to-eat breakfast cereals and baked goods, especially when these food products are produced according to high temperature, short time manufacturing techniques which do not allow for sufficient time for the full generation of grain type flavors. The flavor of the present invention is best described as being bread-crusty, nutty and toasted grain.

The invention is illustrated but not limited by the following examples.

EXAMPLE 1

A fermented malt reaction flavor concentrate was produced from barley malt flour and was incorporated into a bran flake ready-to-eat cereal for flavor evaluation. One hundred pounds of debranned barley malt flour (D-10-F Briess Industries, New York) assayed at 6% maltose was added to 200 pounds of water and to this mixure 50 ml of alpha amylase (termamyl 120L (Novo Labs Inc)) with a 120 KNU/g. Novo standard activity and 50 grams of calcium chloride ($CaCl_2.2H_2O$) were added. The pH of this mixture was determined as 5.25, the mixture was heated to 95° C. and held at that temperature for 35 minutes. Thereafter the mixture was cooled to 60° C. To this mixture was added 101 ml of alpha amylase and 300 ml glucoamylase (AMG 200L Novo Labs Inc of 200 AG/ml Novo standard activity). The mixture was then adjusted to pH 5 were it was held for 2 hours at 60° C. Thereafter the mixture was cooled to 35° C. These two enzymatic treatments hydrolyzed the starch present in the barley malt to produce a sufficient amount of fermentable sugars (assayed at approximately 20% glucose). In the next step the mixture was combined with 2 pounds of active dry yeast *Saccharomyees cerevisiae* (G.B. Fermentation, Feremipan Industries) and the combination was allowed to ferment for 2 hours at a temperature of 35° C. The pH of this mixture was determined to be 4.55. Thereafter the yeast and other enzymes present within the barley malt were inactivated by subjecting the mixture to a temperature of 105° C. for 20 minutes. Next, 100 pounds of unbleached pastry flour which acts as a carrier/drying aid was added and the combination was drum dried at the following conditions: 70 PSI, an approximate temperature of 160° C., 5 RPM drum speed for a period of time of approximately 13.5 seconds. The flow rate was adjusted to dry the material to an approximate 2 percent moisture. The drum was adjusted to a 0.005 inch gap setting. The dough or sponge was placed on the drum and was dried in approximately 10 seconds while in contact with 75% of the drum circumference. For the remaining 3½ seconds while in contact with the other 25% of the drum circumference the dry material was toasted. This heating procedure developed flavor in the fermented malt product by specific condensation, maillard, esterification and other reactions occuring among the hydrolyzed, fermented malt metabolites and autolyzed yeast.

The flavorant produced was then combined with a bran flake formulation where it was incorporated at a level of 2 percent (1% reactive flavor and 1% flour used as a carrier material). This product was compared to a standard cereal product containing the identical ingredients with the exception that the control product contained an equal amount of unfermented malt. The bran flake sample containing the fermented malt reaction flavor concentrate had a more appealing, stronger and superior flavor and taste as compared to the control product.

EXAMPLE 2

A mixture of debranned barley malt flour (D-10-F Briess Industries, New York) assayed at 6% maltose and water at a ratio of 3 to 7 was incubated at 40° C. for 1 hour and then at 70° C. for another hour with constant stirring to inactivate the endogenous enzymes present in the malt. These conditions allowed for the enzymes naturally present within the sponge or dough to further hydrolyze starch present therein and produce sufficient fermentable sugars for the subsequent yeast fermentation. The slurry then was mixed with an additional amount of barley malt flour, vital wheat gluten and yeast to form a dough containing the following ingredients set forth in Table 1. The small amount of vital wheat gluten was added to facilitate the formation and the fermentation of the malt flour dough but the gluten contributed no significant functionality in the final product.

TABLE 1

| Ingredient | Amount |
|---|---|
| Debranned Malt Flour | 1,000 grams |
| Water | 640 grams |
| Vital Wheat Gluten | 50 grams |
| Dry Yeast | 50 grams |

The dough was kneaded and fermented at ambient temperatures for approximately 2½ hours. The fermented dough (pH 4.8) was dried in a drum dryer at a temperature below 150° C. The samples were ground to approximately 30 to 40 mesh particle size. The resulting fermented malt reaction flavor concentrate had a unique bread crust, cooked grain-type flavor. When the flavorant was incorporated at a level of 3.4% dry basis, into a conventional extruded bread crouton, a pleasant, improved flavor was obtained which added to the crouton a more grain type, bready flavor as compared to a control extruded bread crouton product which contained an equivalent amount of unfermented malt flour.

EXAMPLE 3

The yeast fermented malt reaction flavor concentrate was produced in accordance with Example 1 except no carrier was incorporated during drum drying. The flavorant was incorporated into a bread which was compared to a control product containing neither the fermented malt reaction flavor concentrate of this invention nor an unfermented malt flavorant and a bread product containing an equal amount of unfermented malt flour. The formula for these products are set forth below in Table II.

TABLE II

| Ingredients (% wt) | Bread Plus Malt Flour | Bread Plus Fermented Malt Flour | Bread Only |
|---|---|---|---|
| Cake flour | 62.8 | 62.8 | 63.8 |
| Sugar | 3.2 | 3.2 | 3.2 |
| Salt | 1.0 | 1.0 | 1.0 |

TABLE II-continued

| Ingredients (% wt) | Bread Plus Malt Flour | Bread Plus Fermented Malt Flour | Bread Only |
|---|---|---|---|
| Malt flour | 1.0 | — | — |
| Fermented malt reaction flavor | — | 1.0 | — |
| Yeast | 0.4 | 0.4 | 0.4 |
| Water | 31.6 | 31.6 | 31.6 |

The dried ingredients were mixed in a Hobart Blender, the water was added and the ingredients were mixed at speed #1 for 5 minutes and then at speed #2 for 3 minutes. The dough was fermented for one hour at room temperature and then the dough was formed and/or shaped and thereafter proofed for 30 minutes. Then the proofed dough was baked at 190° C. for 30 minutes. A trained test panel consisting of five members evaluated the products on a scale of from 1 to 10 based on the product's yeasty bread flavor. The results are set forth below in Table III.

TABLE III

| Product | Flavor Evaluation Flavor Scale |
|---|---|
| Bread only | 2 |
| Bread plus unfermented malt flour | 5 |
| Bread plus fermented malt reaction flavor | 9 |

EXAMPLE 4

The yeast fermented malt reaction flavor concentrate was produced by a process which utilized enzyme hydrolysis of malt followed by yeast fermentation and autoclaving. 2250 gm debranned barley malt flour (D-10-F Briess Indurstries, NY) was added to 4500 gm of water and to this mixture 2.48 gm $CaCl_2.2H_2O$ and 2.48 ml of alpha amylase (termamyl 120L, Novo Labs, Inc.) were added. The pH of this mixture was determined as 5.29. The mixture was heated in an open kettle to 95° C. and held at that temperature for about 20 minutes. The mixture was cooled to 60° C. To this mixture was added 4.95 ml alpha-amylase and 15 ml glycoamylase (AMG 200L, Novo Labs, Inc.). The mixture was then adjusted to pH 5 where it was held for 2 hours at 60° C. Thereafter, the mixture was cooled to 35° C. In the next step the mixture was combined with 45 gms of active dry yeast *Saccharomyces cerevisiae* (G.B. fermentation, Fermipan Industries) and the combination was allowed to ferment for 2 hours at a temperature of 35° C. The pH of this mixture was determined to be 4.65. Thereafter the yeast and other enzymes present within the system were inactivated by subjecting the mixture to a temperature of 105° C. for 20 minutes in an open kettle. (Inactivation of enzymes can be accomplished during autoclaving. However in the present example it was not possible to autoclave the yeast-fermented malt flour right away, necessitating a separate inactivation step.) Next, the mixture was subjected to a steam heating in an autoclave at temperature of 275° F. (135° C.) and pressure of 23 psi for 30 minutes. After that, the sample was divided into two portions. One was dried in an air flow conventional oven at 50° C. overnight. It was not possible to dry the sample completely with this drying technique due to high hydroscopic material in nature. The dried sample had a moisture content of about 25%. It would be preferable to dry the yeast-fermented, malt flour to less than 10% moisture. The other sample was used "as is" without further removal of water. The slurry had a moisture of 66%.

The above two flavor samples were evaluated in baked goods (bread) and in an extruded dough system.

FLAVOR EVALUATION IN BREAD 1.5% flavorant (dry weight) was incorporated into a bread formula which was compared to a control product containing neither the fermented malt reaction flavor concentrate nor an unfermented malt flour and a bread product containing an equal amount of unfermented malt flour. The formula for these products are set forth below in Table IV.

TABLE IV

FLAVOR EVALUATION IN BREAD

| Ingredient (% Wt) | Bread Only | Bread + Malt Flour | + Fermented malt (dried) | Bread + fermented malt slurry (not Dried) |
|---|---|---|---|---|
| Wheat Flour | 62.8 | 60.5 | 60.5 | 60.5 |
| Sugar | 3.2 | 3.2 | 3.2 | 3.2 |
| Salt | 1.0 | 1.0 | 1.0 | 1.0 |
| Shortening | 2.0 | 2.0 | 2.0 | 2.0 |
| Malt Flour* | — | 1.5 | — | — |
| Dried Fermented Malt* | — | — | 1.8 | — |
| Not Dried Fermented Malt* | — | — | — | 4.0 |
| Yeast | 0.4 | 0.4 | 0.4 | 0.4 |
| Water | 30.6 | 31.4 | 31.3 | 28.9 |

*These are same amount of malt flavor on dry weight basis

Bread Preparation

The straight dough method was used to make the bread. All the ingredients except yeast and water were mixed in a Hobart Blender for about 5 minutes, the water was added and the mixture was mixed at Speed #1 for 3 minutes and then yeast (Fermipan active dried yeast) was added. The mixing continued at Speed #1 for 2 minutes and at speed #2 for 5 minutes. The dough was fermented for one hour at room temperature and then the dough was formed and/or shaped and thereafter proofed for 30 minutes. Then the proofed dough was baked at 190° C. for 30 minutes. The baked bread was evaluated after 30 minutes cooling from oven by a trained panel on a scale of from 1 to 10 based on the product's yeast bread flavor. The results are set forth below in Table V.

TABLE V

FLAVOR EVALUATION

| Product | Score (Flavor Scale) |
|---|---|
| Bread only | 2 |
| Bread + malt flour | 4 |
| Bread + fermented malt (dried) | 9 |
| Bread + fermented malt slurry (not dried) | 9 |

Flavor Evaluation in the Extruded Product

A 2% (dry weight basis) of yeast fermented malt reaction flavor concentrate (either dried or not dried after autoclave heating) was incorporated into wheat flour and then subjected to a high temperature high shear extrusion process. Two controls were prepared; (1) wheat flour alone and (2) 2% regular malt (unfermented) with wheat flour. Both controls were subjected to the same extrusion conditions in a Werner & Pfleiderer (W/P) Contina 37 twin screw co-rotation extruder. The extruder was set up with a five section barrel with the temperature controlled as follows: #1 50° C., #2 65° C., #3 85° C., #4 105° C. and #5 105° C. (nearest to the die) respectively. The die consisted of one insert with 5/64" diameter circular opening. The dry feed rate and the water feed rate were set at 15 Kg/hr and 2.5 Kg/hr respectively. The extrudate was tempered for about 20 minutes at room temperature after exit from the extruder. The extrudate was then sized to ¼" pieces with Fitz Mill without screen. The sample was then dried/toasted at 275° F. (135° C.) for about 20 minutes in a conventional air oven. The samples were evaluated by a trained panel of five members to determine the flavor characteristics. The extrudate containing the fermented malt reaction flavor concentrate (either dried or not dried) had a more appealing and stronger cooked grain-like flavor. The flavor and taste was nutty and bready as compared to the control.

What is claimed is:

1. A process for producing a heat-stable, yeast fermented malt reaction flavor concentrate which is of low volatility from a mixture consisting essentially of malt flour, yeast and 6 to 30% fermentable sugar based on the malt which comprises:
   (a) preparing a malt flour for yeast fermentation;
   (b) fermenting the fermentable sugars present within the malt flour with yeast in a water medium wherein the yeast is added at a concentration of from 0.5% to 10% based upon the total weight of the malt flour and water present therein at a temperature of from about 10° C. to about 60° C. for a period of time from ½ hour to 6 hours; and
   (c) heating the fermented malt produced in step (b) at a temperature and for a period of time sufficient to inactive the yeast and any enzymes present and to develop flavor within said fermented malt said heating comprising autoclaving at 120° C. to 200° C. for a period of time from 3 to 45 minutes.

2. The process according to claim 1 wherein the prepared malt flour has present therein from 6% to 30% fermentable sugars.

3. The process according to claim 2 wherein the prepared malt flour has 10% to 20% fermentable sugars.

4. The process according to claim 1 wherein the yeast concentration is from 1% to 7%.

5. The process according to claim 4 wherein the concentration is from 2% to 5%.

6. The process according to claim 1 wherein the temperature of step (b) is from 20° C. to 35° C.

7. The process according to claim 6 wherein the period of time is from 2 to 4 hours.

8. The process according to claim 1 wherein the preparation of the malt flour for yeast fermentation comprises milling the malt flour, steeping in water and hydrolyzing starch present within said flour with endogenous enzymes present within said flour to yield sufficient fermentable sugars.

9. The process according to claim 8 wherein the steeped malt at a slurry concentration of from 20% to 70% is subjected to a temperature of from 30° C. to 45° C. for from 30 minutes to 150 minutes.

10. The process according to claim 1 wherein the preparation of the malt flour for yeast fermentation comprises adding exogenous glycolytic enzymes to a milled, steeped malt flour to hydrolyze starch present within said flour to yield sufficient fermentable sugars.

11. The process according to claim 10 wherein the glycolytic enzymes are alpha amylase, glucoamylase or combinations thereof and wherein the starch present within said malt flour is gelatinized starch.

12. The process according to claim 1 wherein the preparation of the malt flour for yeast fermentation comprises milling the malt flour, steeping in water and adding exogenous fermentable sugars.

13. The process according to claim 1 wherein the prepared malt is a caramel malt containing from 10% to 18% fermentable sugars.

14. The process according to claim 1 wherein the autoclaved fermented malt is subsequently dried to a moisture content less than 10%.

15. The process according to claim 1 wherein the malt flour is derived from a cereal grain selected from the group consisting of rye, barley, wheat and combinations thereof.

* * * * *